United States Patent [19]

Schwarzberg

[11] 4,272,506

[45] Jun. 9, 1981

[54] PURIFICATION OF REAGENTS BY DISULFIDE IMMOBILIZATION

[75] Inventor: Moshe Schwarzberg, Hastings on Hudson, N.Y.

[73] Assignee: Syva Company, Palo Alto, Calif.

[21] Appl. No.: 71,526

[22] Filed: Aug. 31, 1979

[51] Int. Cl.³ .......................... C07G 7/00; C12Q 1/00; G09K 11/07; G01N 33/52

[52] U.S. Cl. .................................... 424/8; 23/230 B; 250/302; 260/112 R; 260/112 B; 424/1; 424/12; 424/13; 424/85; 424/88; 424/177; 424/180; 435/4; 435/7

[58] Field of Search ..................... 424/1, 8, 12, 13, 85, 424/88, 177, 86, 87, 89, 92; 23/230 B; 250/302; 260/112 R, 112 B; 435/4, 7

[56] References Cited

U.S. PATENT DOCUMENTS

| | | | |
|---|---|---|---|
| 3,652,761 | 3/1972 | Weetall | 424/12 |
| 3,690,834 | 9/1972 | Goldstein | 424/12 X |
| 3,998,943 | 12/1976 | Ullman | 424/12 |
| 4,039,652 | 8/1977 | Adams | 424/8 X |
| 4,160,016 | 7/1979 | Ullman | 424/12 X |
| 4,176,006 | 11/1979 | Cormier | 435/174 X |

Primary Examiner—Anna P. Fagelson

Attorney, Agent, or Firm—Bertram I. Rowland

[57] ABSTRACT

A method is provided for preparing immunoassay reagents involving labeled members of specific binding pairs substantially enriched relative to contaminating labeled materials. The method involves conjugating a member of a specific binding pair to a support by a covalent bond which is cleavable under mild conditions to provide a binding pair member-support conjugate. Combining the binding pair member-support conjugate with a labeled composition containing the reciprocal member of the binding pair, so that the labeled reciprocal member becomes bound to the support through the binding of the specific binding pair. Separating the support to which is bound the labeled member from the remaining labeled material and then cleaving the bond joining the labeled specific binding pair to the support to provide labeled reagent for immunoassays. In particular, an antibody is linked to a support by disulfide linkage and a composition containing the reciprocal antigen to the antibody is labeled with a chromophore, particularly fluorescer. The support is freed of labeled material other than the desired labeled antigen and the disulfide link cleaved to provide labeled reagent for immunoassays.

10 Claims, No Drawings

PURIFICATION OF REAGENTS BY DISULFIDE IMMOBILIZATION

BACKGROUND OF THE INVENTION

1. Field of the Invention

Immunoassays provide a technique for measuring specific compounds by employing the properties of anti-bodies or other receptors, which recognize a specific polar and spatial organization of an antigen. In many instances, the antibodies and antigens are obtained as complex mixtures of proteins, where the compounds of interest may be present in minor amount and in some instances an extremely small proportion of the total proteins present.

The immunoassays depend upon the ability to label one of the members of the specific binding pair—antigen and homologous antibody—with a label which provides a detectible signal. The methods then provide for distinguishing between the amount of the labeled member of the specific binding pair bound to its reciprocal member and unbound labeled member.

In many assays, no separation is involved when distinguishing between bound and unbound labeled member. To the extent that the labeled member is accompanied with other labeled material, this additional label provides a background signal which reduces the sensitivity and accuracy of the assay. Even where a separation step is involved, in many instances, it will be useful to minimize the presence of contaminating labeled material.

It is therefore desirable to provide a method for obtaining reagents involving labeled members of specific binding pairs substantially free of other labeled material. Any such technique must not adversely affect the immunological properties of the reagent. In addition, the technique should allow for concentration and isolation of the desired material in a form useful for immunoassays.

2. Description of the Prior Art

U.S. Pat. Nos. 3,998,943 and 3,996,345 describe immunoassay techniques employing chromophores as labels for providing a detectible signal.

SUMMARY OF THE INVENTION

A method is provided for preparing labeled reagents for immunoassays. An insoluble support having a plurality of mercapto groups is activated by reacting the mercapto groups with a functionality which allows for reaction with a second mercapto group to produce a disulfide linkage. A composition containing one of the members of a specific binding pair—antigen and its homologous antibody—is modified to introduce mercapto groups, if such mercapto groups are not naturally present. The mercapto group containing composition is combined with the activated support to provide for the binding of the member of a specific binding pair to the support through disulfide links. A second composition having the reciprocal member of the specific binding pair is labeled with labels capable of providing a detectible signal, the labels being in sufficient amount to ultimately insure a desired signal level. The labeled composition is then combined with the support composition, where the binding pair members bind, so that the labeled member is now bound to the support through the intermediary of the other member of the specific binding pair. The support is washed to remove non-specifically bound material, followed by cleavage of the disulfide linkage to provide labeled reagents for use in immunoassays.

DESCRIPTION OF THE SPECIFIC EMBODIMENTS

In accordance with the subject invention, labeled reagents can be prepared by covalently bonding an immunological pair member, ligand or its homologous antiligand, to an insoluble support by means of a spacer arm which includes a disulfide linkage in the spacer arm chain. The other member of the specific binding pair, which is labeled with an appropriate label, and is generally part of a complex mixture, is combined with the reciprocal member bound to the support, so as to produce the immunological pair member complex. The solid support is then washed to remove non-specifically bound material, followed by cleavage of the disulfide linkage to release the immunological pair complex, which may be used as a reagent in diagnostic assays, for histochemical staining, or the like.

In describing the subject invention, the method of preparation of the reagents will be considered first. Within this category, will be the formation of the gel with an activated disulfide containing spacer arm, the mercapto functionalization of the immunological pair member, the binding of the mercapto functionalized immunological pair member to the gel, the labeling of the reciprocal pair member, the combining of the labeled reciprocal pair member with its homologous member bound to the support to form the complex, and the isolating of the complex which is enriched relative to labeled material which is not involved in the complex. In addition, the use of the subject compositions will be illustrated for diagnostic assays.

The labeled complexes of the subject invention involve the non-covalent binding of two immunogens, ligand and receptor, normally an antibody, where the receptor specifically binds to a particular spatial and polar organization of its homologous or reciprocal ligand. In the subject complex, either the ligand or the receptor (hereinafter referred to as "antiligand") may be labeled with a label capable of providing a detectable signal. The ligand will normally be immunologically polyvalent, that is, have a plurality of epitopic or determinant sites, and will be referred to as an antigen or antigenic. Therefore, the complex of the ligand and the antiligand, will leave at least one free epitopic site on the ligand, and generally more than one site, while normally fewer than about 50% of the available epitopic sites on the antigen will be bound to antiligand.

METHOD OF PREPARATION

In preparing the complexes of the subject invention, an insoluble support or gel will be employed, which allows for isolation of the complex, free of labeled compounds which are not members of the subject complex; that is, free of labeled members which are not specifically bound to the gel.

Various inert insoluble polymeric materials may be employed, which have functionalities or can be functionalized to provide a spacer arm. The gel or support may be naturally occurring or synthetic and may be modified to provide for convenient functionalities for linking the spacer arm as appropriate. Illustrative polymers include agarose, Sepharose, Sephadex, polyacrylamide, polystyrene, or the like, which may be functionalized with amino groups, carboxyl groups, active olefins, or the like. Conveniently, commercially available materials may be employed, such as Affi-gel 401, supplied by Bio-Rad Laboratories, Inc., which is an agarose polymer substituted with N-acetyl cysteinylamidopropyl groups.

The spacer arm to the disulfide linkage may be a bond, but will usually have at least about two atoms, and not more than about 20 atoms, usually from about 4 to 16 atoms, which are carbon, oxygen, and nitrogen, wherein oxygen is present as oxy or non-oxo carbonyl and nitrogen is present as amino or amido, preferably bonded solely to carbon, except when nitrogen is amido, with the disulfide bonded to aliphatically saturated carbon. The spacer arm is not critical to the subject invention, although depending upon the nature of the gel or support, different links may be desired. Desirably, the spacer arm will be neutral, rather than carrying an ionic charge.

The mercapto group is then activated by forming a bond between the sulfur and an electrophilic leaving group, usually sulfur to form a disulfide linkage. The disulfide linkage is usually a mixed disulfide, which is readily displaced by a mercaptide group. The disulfide may be bonded to sulfite, cyano, an aryl group, or other group which provides for ready substitution by a mercaptide to form a disulfide link to the member of the specific binding pair. Illustrative aryl groups include 2-pyridyl, 2,4-dinitrophenyl, and the like. The activating group should permit ready substitution by the mercapto groups of the immunological pair member, so as to provide for efficient bonding of the immunological pair member to the support. Normally, there will be a substantial excess of the disulfide bonded to the support as compared to the amount of the immunological pair member which becomes bound to the support.

Where the immunological pair member does not have naturally available mercapto groups and even in some situations where it does, mercapto groups will be introduced into the molecule. Various compounds may be employed having an available sulfur for disulfide formation. Illustrative compounds include S-acetyl mercaptosuccinic anhydride and S-propenyl 2-mercaptoglutaric anhydride. These compounds will be reacted under conventional conditions with the immunological pair member to introduce on the average at least one mercapto group per mole of immunological pair member and generally not more than ten mercapto groups per member, usually on the average from about 1.5 to 5 mercapto groups per mole of member. During the preparation of the mercapto substituted immunological pair member, air should be excluded to prevent disulfide formation.

A wide variety of ligands and antiligands may be modified by the introduction of mercapto groups for linking to the support by disulfide linkage. The following is illustrative of the variety of ligands and receptors which may be involved.

ANALYTE

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
   $\alpha_1$-glycoprotein
$\alpha_1$X-Glycoprotein
Thyroxin-binding globulin
Inter-$\alpha$-trypsin-inhibitor
Gc-globulin
   (Gc 1-1)
   (Gc 2-2)
   (Gc 2-2)
Haptoglobin
   (Hp 1-1)
   (Hp 2-1)
   (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen Plasminogen
$\beta_2$-glycoprotein I
$\beta_2$-glycoprotein II
Immunoglobulin G
    (IgG) or $\gamma$G-globulin
Mol. formula:
    $\gamma_2\kappa_2$ or $\gamma_2\lambda_2$
Immunoglobulin A (IgA)
    or $\gamma$A-globulin
Mol. formula:
    $(\alpha_2\kappa_2)^n$ or $(\alpha_2\lambda_2)^n$
Immunoglobulin M
    (IgM) or $\gamma$M-globulin
Mol. formula:
    $(\mu_2\kappa_2)^5$ or $(\mu_2\lambda_2)^5$
Immunoglobulin D(IgD)
    or $\gamma$D-Globulin ($\gamma$D)
Mol. formula:
    $(\delta_2\kappa_2)$ or $\delta_2\lambda_2)$
Immunoglobulin E (IgE)
    or $\gamma$E-Globulin ($\gamma$E)
Mol. formula:
    $(\epsilon_2\kappa_2)$ or $(\epsilon_2\lambda_2)$
Free $\kappa$ and $\lambda$ light chains
Complement factors:
C'1
    C'1q
    C'1r
    C'1s
C'2
C'3
    $\beta_1$A
    $\alpha_2$D
C'4
C'5
C'6
C'7
C'8
C'9
Important blood clotting factors include:

| BLOOD CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
    (parathromone)
Thyrocalcitonin
Insulin
Glucagon
Relaxin
Erythropoietin
Melanotropin
    (melanocyte-stimulating hormone; intermedin)
Somatotropin
    (growth hormone)
Corticotropin
    (adrenocorticotropic hormone)
Thyrotropin
Follicle-stimulating hormone
Luteinizing hormone
    (interstitial cell-stimulating hormone)
Luteomammotropic hormone
    (luteotropin, prolactin)
Gonadotropin
    (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
    CRF, LRF, TRF, Somatotropin-RF,
    GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and turberculin |
| Klebsiella aerogenes | Polysaccharide |
| Klebsiella cloacae | Polysaccharide |
| Salmonella typhosa | Lipopolysaccharide, Polysaccharide |

| Species of Microorganisms | Hemosensitin Found in |
|---|---|
| Salmonella typhi-murium; | Polysaccharide |
| Salmonella derby | |
| Salmonella pullorum | |
| Shigella dysenteriae | Polysaccharide |
| Shigella flexneri | |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
    *Corynebacterium diptheriae*
Pneumococci
    *Diplococcus pneumoniae*
Streptococci
    *Streptococcus pyogenes*
    *Streptococcus salivarus*
Staphylococci
    *Staphylococcus aureus*
    *Staphylococcus albus*
Neisseriae
    *Neisseria meningitidis*
    *Neisseria gonorrheae*
Enterobacteriaciae

*Escherichia coli*
    *Aerobacter aerogenes* } The coliform bacteria
    *Klebsiella pneumoniae*
    *Salmonella typhosa*
    *Salmonella choleraesuis* } The Salmonellae
    *Salmonella typhimurium*
    *Shigella dysenteriae*
    *Shigella schmitzii*
    *Shigella arabinotarda*
    *Shigella flexneri* } The Shigellae
    *Shigella boydii*
    *Shigella Sonnei*

Other enteric bacilli
    *Proteus vulgaris*
    *Proteus mirabilis* } Proteus species
    *Proteus morgani*
    *Pseudomonas aeruginosa*
    *Alcaligenes faecalis*
    *Vibrio cholerae*

Hemophilus-Bordetella group
    *Hemophilus influenzae,*    H. ducreyi
                                           H. hemophilus
                                           H. aegypticus
                                           H. parainfluenzae
    *Bordetella pertussis*

Pasteurellae
    *Pasteurella pestis*
    *Pasteurella tulareusis*

Brucellae
    *Brucella melitensis*
    *Brucella abortus*
    *Brucella suis*

Aerobic Spore-forming Bacilli
    *Bacillus anthracis*
    *Bacillus subtilis*
    *Bacillus megaterium*
    *Bacillus cereus*

Anaerobic Spore-forming Bacilli
    *Clostridium botulinum*
    *Clostridium tetani*
    *Clostridium perfringens*
    *Clostridium novyi*
    *Clostridium septicum*
    *Clostridium histolyticum*
    *Clostridium tertium*
    *Clostridium bifermentans*
    *Clostridium sporogenes*

Mycobacteria
    *Mycobacterium tuberculosis hominis*
    *Mycobacterium bovis*
    *Mycobacterium avium*
    *Mycobacterium leprae*
    *Mycobacterium paratuberculosis*

Antinomycetes (fungus-like bacteria)
    *Actinomyces israelii*
    *Actinomyces bovis*
    *Actinomyces naeslundii*
    *Nocardia asteroides*
    *Nocardia brasiliensis*

The Spirochetes
    *Treponema pallidum*      *Spirillum minus*
    *Treponema pertenue*     *Streptobacillus moniliformis*
    *Treponema carateum*
    *Borrelia recurrentis*
    *Leptospira icterohemorrhagiae*
    *Leptospira canicola*

Mycoplasmas
    *Mycoplasma pneumoniae*

Other pathogens
    *Listeria monocytogenes*
    *Erysipelothrix rhusiopathiae*
    *Streptobacillus moniliformis*
    *Donvania granulomatis*
    *Bartonella bacilliformis*

Rickettsiae (bacteria-like parasites)
    *Rickettsia prowazekii*
    *Rickettsia mooseri*
    *Rickettsia rickettsii*
    *Rickettsia conori*
    *Rickettsia australis*
    *Rickettsia sibiricus*
    *Rickettsia akari*
    *Rickettsia tsutsugamushi*
    *Rickettsia burnetii*
    *Rickettsia quintana*

Chlamydia (unclassifiable parasites bacterial/viral)
    Chlamydia agents (naming uncertain)

Fungi
    *Cryptococcus neoformans*
    *Blastomyces dermatidis*
    *Histoplasma capsulatum*
    *Coccidioides immitis*
    *Paracoccidioides brasiliensis*
    *Candida albicans*
    *Aspergillus fumigatus*
    *Mucor corymbifer (Absidia corymbifera)*
    *Rhizopus oryzae*
    *Rhizopus arrhizus* } Phycomycetes
    *Rhizopus nigricans*
    *Sporotrichum schenkii*
    *Fonsecaea pedrosoi*
    *Fonsecaea compacta*
    *Fonsecaea dermatidis*
    *Cladosporium carrionii*
    *Phialophora verrucosa*
    *Aspergillus nidulans*
    *Madurella mycetomi*
    *Madurella grisea*
    *Allescheria boydii*
    *Phialosphora jeanselmei*
    *Microsporum gypseum*
    *Trichophyton mentagrophytes*
    *Keratinomyces ajelloi*
    *Microsporum canis*
    *Trichophyton rubrum*
    *Microsporum andouini*

Viruses

Adenoviruses

Herpes Viruses
    Herpes simplex
    Varicella (Chicken pox)

-continued

Herpes Zoster (Shingles)
Virus B
Cytomegalovirus
Pox Viruses
Variola (smallpox)
Vaccinia
Poxvirus bovis
Paravaccinia
*Molluscum contagiosum*
Picornaviruses
Poliovirus
Coxsackievirus
Echoviruses
Rhinoviruses
Myxoviruses
Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus
Arboviruses
Eastern Equine Eucephalitis Virus
Western Equine Eucephalitis Virus
Sindbis Virus
Chikugunya Virus
Semliki Forest Virus
Mayora Virus
St. Louis Encephalitis Virus
California Encephalitis Virus
Colorado Tick Fever Virus
Yellow Fever Virus
Dengue Virus
Reoviruses
Reovirus Types 1-3
Hepatitis
Hepatitis A Virus
Hepatitis B Virus
Tumor Viruses
Rauscher Leukemia Virus
Gross Virus
Maloney Leukamia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids, their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steriod mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their matabolites.

The next group of drugs is aminoalkylbenzenes, with alkyl of from 2 to 3 carbon atoms, which includes ephedrine, L-dopa, epinephrine, narceine, papverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procainemide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyroine, oxytocin, ACTH, angiotensin, met-and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE, and IgM, the molecular weights will generally vary from about 160,000 to about $10^6$. Enzymes will normally range from about 10,000 to 6000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

As the other member of the complex, the reciprocal member of the ligand-antiligand pair will be labeled with a label which is a member of a signal producing system. Various labels may be employed and have been employed for immunoassays. Such labels include catalysts, particularly enzymes, chromophores—dyes, fluorescers, chemiluminescers, and phosphors—and the like.

Of particular interest in the subject invention are chromogenic compounds, which are either a dye absorbing above 350 nm or a fluorescer which also absorbs above 350 nm, preferably about 400 nm, and more preferred above 450 nm and emits lights of a wavelength at least about 10 nm greater than the light absorbed. Various chromophores may be employed and will be linked to the member of the specific binding pair by conventional means. Usually, there will be on the average at least one chromophore per molecule, and usually not more than about one per 2,000 molecular weight, more usually not more than about one per 5,000 molecular weight, and frequently not more than about one per 10,000 molecular weight.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine-0, 2-(9'-anthroyl)palmitate, dansyl phosphatidylethanolamine, N,N'-dioctadecyl oxacarboxyanine, N,N'-dihexyl oxacarbocyanine, merocyanin, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene)bis-benzoxazole, p-bis[2-(4-methyl-5-phenyloxazolyl)]benzene, 6-dimethylamino-1,2-benzophenazin, retinol, bis(3'-aminopyridinium) 1,10-decandiyldiiodide, sulfonaphthyl hydrazone of hellebrigenin, chlortetracycline, N-(7-dimethylamino-4-methyl-2-oxo-3-chromenyl) maleimide, N-[p-(2-benzimidazoyl)-phenyl] maleimide, N-(4-fluoranthyl) maleimide, bis(homovanillic acid), resazurin, 4-chloro-7-nitro-2.1.3-benzooxadiazole, merocyanine 540, resorufin, rose bengal, 2,4-diphenyl-3(2H)-furanone, and rare earth chelates.

The manner of labeling is conventional, many chromophores being commercially available with active functionalities for linking to antigens and antibodies or readily susceptible of having such functionalities introduced.

The other label of particular interest is enzymes. Various enzymes may be employed, which have been extensively described in a number of patents. See for example U.S. Pat. No. 3,817,837.

In preparing the complex of the subject invention, an appropriate insoluble support having a plurality of mercapto functionalities is activated by forming the alkali metal mercaptide and combining the resulting mercaptide with an active diaryl disulfide in an inert atmosphere. The resulting gel having the aryl disulfide groups is then combined with the mercapto containing member of the specific binding pair, where the equivalent of the disulfide on the gel is in excess of the number of moles of the specific binding pair member. The reaction is carried out under mild conditions in an aqueous medium for a time sufficient for the mercapto groups of the specific binding pair member to displace an aryl mercapto group.

After freeing the gel of non-covalently bound material, the labeled reciprocal member of the specific binding pair is combined with the gel, to which is bound the mercapto containing member of the specific binding pair, under mild conditions for a sufficient time for ligand-antiligand complex formation. The gel is then freed of any non-specific binding by protein, particularly of labeled protein which was present in admixture with the labeled member of the specific binding pair. Conveniently, this can be carried out by careful washing.

The disulfide is then cleaved in accordance with conventional techniques, for example using dithioerythritol or mercaptoethanol, or the like. Normally, the sulfur reductant will be used in substantial excess. The resulting complex which is freed from the column is then purified by conventional means, such as dialysis, filtration, centrifugation, washing, or the like.

The resulting chromophore containing reagents can be used in a variety of ways, where immunological complexes are involved employing a chromophore label. In particular, the reagents find use in assays for antigens or antibodies as described in U.S. Pat. No. 3,996,345. The appropriate portions, col. 17, line 60 to col. 23, line 50 describing the assay method in this patent are incorporated herein by reference. Therefore, the method will only be described in limited detail. In the method, the complex is employed as the fluorescent reagent, having fluorescer indirectly bound to antigen. The fluorescent reagent is combined with the sample containing the antigenic analyte either prior to or simultaneously with the combining of the analyte to antibody labeled with quencher. By quencher is intended a molecule which can accept energy from the excited fluorescer molecule, when within a predetermined distance, usually under 100 Å, so that the fluorescer does not emit light. By having a competition between the ligand bound to fluorescer and the analyte ligand for quencher conjugated antibody, the amount of observed flourescence will be related to the amount of analyte in the medium.

In the subject invention, the reagent is the fluorescer conjugated antigen bound to receptor, which still retains a plurality of determinant sites, while substantially free of fluorescent bound protein other than the ligand-labeled receptor complex.

In order to further demonstrate the subject invention, the following examples were carried out. The following examples are offered by way of illustration, and not by way of limitation.

EXPERIMENTAL

All temperatures not otherwise indicated are in centigrade. All percents and parts not otherwise indicated are by weight, except for mixtures of liquids, which are by volume. The following abbreviations are employed:

DTE—dithioerythritol; DMF—N,N-dimethyl formamide, DTNB—2-carboxy-4-nitrothiophenol; EDTA—ethylene diaminetetraacetic acid; Tris—trimethylol-methylamine; FITC—fluoresceinisothiocyanate; RITC—rhodamineisothiocyanate; PMS—phenazine methosulfate; RID—radial immunodiffusion; AT—$\alpha_1$-antitrypsin.

EXAMPLES

Ex. 1. Preparation of Sheep Anti-HuIgA ($\alpha$ chain specific)

Antiserum (sheep anti-HuIgA, 100 ml) was stirred with 250 mg human Cohn fraction II (Miles) overnight in the cold. The solids were removed by centrifugation and the supernatant IgG was precipitated by 50% saturation with ammonium sulfate. The precipitate was collected by centrifugation and redissolved in 50 ml of 0.1 M sodium acetate buffer at pH 5.5. The solution was dialyzed overnight against the same buffer (1 l.), some turbidity which appeared was removed by centrifugation and the pH of the supernatant adjusted to 8.0 by the addition of solid $K_2HPO_4$. IgG antibody was again precipitated by 50% ammonium sulfate, collected by centrifugation and redissolved and dialyzed against acetate buffer as before. The resulting solution was 50 ml and protein estimated by UV was 35.7 mg/ml ($E^{1\%}=14$).

Ex. 2. Preparation of Thiol labelled Sheep Anti-HuIgA

Anti-HuIgA (2 ml, 35.7 mg/ml) was made 0.1 M in potassium phosphate and 2 mM in EDTA at pH 7.4. A solution of S-acetylmercaptosuccinic anhydride, 0.6 mg in 0.08 ml dry DMF was added slowly (approx. 2 min.) at room temperature with good stirring. After an additional 10 min., a solution of 0.2 ml of 0.5 M $NH_2OH$ at pH 7.4 (freshly prepared) was added and stirred for 5 min. The pH of the reaction mixture was reduced to 5.2 by the addition of solid L-malic acid and immediately applied for separation on Sephadex G-25 (0.9×25 cm). The Sephadex column was prepared well in advance from degassed Sephadex and equilibrated with 0.1 M $K_2HPO_4$ containing 2 mM EDTA (at pH 5.2) degassed and saturated with argon. The eluted protein, about 4.0 ml was immediately taken for reaction with the "activated" gel for immobilization. In another experiment this method was shown to give 2–3 groups of SH per IgG molecule.

Ex. 3. Preparation of "Activated" Gel

Affigel-401 (SH, from Bio-Rad, 4–6 $\mu$mole/ml) was used. Packed gel (3.5 ml wet) was washed briefly with deionized water and suspended in 20 ml water containing 50 mg sodium borohydride. After 1 hr. at room temperature the gel was washed consecutively with 30–50 ml each of $H_2O$, 0.01 M acetic acid, $H_2O$, and 0.1 M potassium phosphate buffer containing 2 mM EDTA at pH 7.8. (All filtrations and washes were made on a Buchner funnel with Whatman filter paper and water aspirator vacuum resulting in a 2 drops/5 sec. rate. All solutions were degassed and saturated with argon before use.) To the packed gel a solution of DTNB was added and the mixture shaken for 20 min. at room temperature (DTNB solution-dissolve 8 mg of DTNB in 0.3 ml methanol, add 3 ml of phosphate buffer and adjust the pH to 7.8 by adding solid Tris base). The gel was then washed extensively with phosphate buffer until no DTNB was detected (test with DTE).

Ex. 4. Coupling of Thiol Labeled Antibody to "Activated" Gel

Gel (1.75 ml) was mixed with 2 ml of Thiol labeled antibody and 2 ml potassium phosphate buffer. The pH of the mixture was adjusted to 8.0 by the addition of Tris base. After 36 hrs. the gel was washed with potassium phosphate containing 0.33 M NaCl until $OD_{280}$ of the wash was >0.01. The collected solution and wash were dialyzed overnight against phosphate buffer to permit the determination of unbound protein by UV. The results indicated about 9.0 mg of protein in the wash implying by subtraction about 20 mg of antibody protein being bound to the gel.

Ex. 5. Preparation of Flourescein-labelled IgA Fraction

A crude extract of IgA from human Cohn fraction III (56 ml) was concentrated to 4.8 ml at which time the protein concentration estimated by UV ($E^{1\%}=14$) was 40.5 mg/ml. The crude extract was obtained by suspending 5 gm. Cohn fraction III (Miles) for 30 min. in 300 ml 0.05 M Sodium phosphate-0.2 M sodium chloride buffer, pH 8.0. The mixture was centrifuged to remove undissolved protein and the supernatant was dialyzed against 3 changes of deionized water over 3 days. A heavy precipitate was removed by centrifugation. The pH of the solution was adjusted to 7.6 by the addition of solid $NaHCO_3$ and then raised to 9.0 by the addition of $Na_2CO_3$. The protein was labeled with FITC (8.0 mg in 0.5 ml dry DMF) for 3 hrs. at room temperature. The mixture was separated on Sephadex G-25 (0.9×25 cm) equilibrated with 0.05 M $KPO_4$ buffer containing 2 mM EDTA at pH 8.0. Since the capacity of the column was small, separation was done in two portions (2.4 ml of reaction mixture each). The collected conjugate, 8.5 ml, had 24.6 mg/ml protein estimated by UV ($E^{1\%}=14$), about 2.6 mg/ml IgA estimated by RID (Meloy kit) and the degree of labeling was 10.4 mole/mole.

Ex. 6. Absorption of Fluorescein-labelled IgA by the antibody-bound Gel and Elution of the IgA:anti-IgA Complex The antibody-bound gel (1.75 ml) was incubated with 3.0 ml of the fluorescein labeled IgA solution for 4 hrs. at room temperature with gentle shaking. The gel was separated by filtration on a Buchner funnel and washed with 0.1 M potassium phosphate—0.33 M NaCl—2 mM EDTA buffer at pH 8.0 until no protein could be detected in the wash. The antibody-IgA complex was then eluted by reduction of the disulfide bond with DTE (dithioerythritol) in the following manner. The gel was shaken for 20 min. at room temperature with 3 ml of $PO_4$/NaCl/EDTA buffer containing 5 $\mu$moles DTE, then filtered and washed with 10 ml buffer. This procedure was repeated 2X but with 10 $\mu$mole DTE in the buffer instead of 5 $\mu$mole, as applied in the first extraction. The three DTE extract solutions were dialyzed overnight against 4 l of 0.05 M potassium phosphate—0.15 M NaCl—2.5 mM EDTA—0.25% $NaN_3$ at pH 8.0. The protein content was then estimated from the absorption spectra. IgA was estimated from the absorption of the fluorescein at 493 nm, assuming as an approximation the same ratio of $OD_{493}/OD_{280}$ for the eluted IgA as for the crude IgA (before absorption). Table I describes the results obtained.

TABLE I

CHARACTERIZATION OF ANITBODY-IgA COMPLEX ELUTED FRACTIONS

| Fraction no. | Final Volume (ml) | Protein (mg/ml) | IgA (mg/ml) |
|---|---|---|---|
| 1 | 14 | 0.66 | 0.2 |
| 2 | 11 | 0.98 | 0.26 |
| 3 | 11 | 0.19 | 0.042 |

Ex. 7. Preparation of rhodamine-labeled anti-human IgA

A. To one hundred ml of sheep anti-human IgA was added 250 mg of IgG (Cohn fraction II, Miles Lab.) and the mixture stirred overnight in the cold. The resulting precipitate was removed by centrifugation. To the supernatant was added 50 ml saturated ammonium sulfate solution in the cold with stirring. The resultant precipitate was separated by centrifugation and redissolved in 50 ml of 0.1 M sodium acetate buffer at pH 5.5 After dialysis against the same buffer (1 l.) for 24 hrs., a small amount of precipitate was formed which was removed by centrifugation. The pH of the supernatant was adjusted to 8.0 by the addition of solid $K_2HPO_4$ and the globulins were reprecipitated by the addition of 25 ml saturated ammonium sulfate solution. The resultant precipitate was separated by centrifugation, redissolved in 0.1 M sodium acetate buffer at pH 5.8 and dialyzed against 2×1 l. of the same buffer for 2 days. Protein was estimated by UV at 35.7 mg/ml (assume $E_{280}^{1\%}=14$).

B. To 0.3 ml of the antibody solution prepared above was added 0.12 ml glycerol and the pH adjusted to 9.5 by the addition of solid $Na_2CO_3$. A solution of 0.75 mg of tetramethylrhodamine isothiocyanate (Baltimore Biological Lab.) in 50 μl dry dimethylformamide was added slowly and the solution stirred for 3 hrs. at room temperature. The solution was then separated by application to a column (0.9×15 cm) of Sephadex LH-20 equilibrated with buffer consisting of 7 parts of 0.04 M potassium phosphate buffer containing 0.05% $NaN_3$, at pH 8.0, and 3 parts of glycerol. The red protein band (first band eluted) was collected.

Ex. 8. Standard curve for Human IgA and Assay

The protocol for the IgA assay is as follows. The assay buffer is 0.01 M PBS (0.15 M NaCl) plus 2% PEG 6000, pH 8.0. An assay mixture is prepared as follows. Into a vial is introduced 25 μl of the sample or buffer+250 μl buffer, followed by 25 μl of the fluorescent reagent+250 μl buffer+25 μl of the quencher reagent+250 μl buffer, the mixture vortexed for 2-3 sec. followed by a 10 min. incubation at RT. The mixture is then diluted with 2 ml buffer and vortexed 2-3 sec. The fluorescent working solution was fraction 2, Ex. 6 diluted 1:8. Quencher antibody was diluted 1:15. Calibrators were prepared by serial dilutions of Meloy reference serum. Specimens were diluted 1:11 before assay. The results obtained were compared with RID values determined by another laboratory.

TABLE II

ASSAY FOR IgA IN PATIENT SERUMS IgA(mg/ml)

| RID | Fluorescence |
|---|---|
| 1.79 | 1.48 |
| 2.80 | 2.53 |
| 1.10 | 0.88 |
| 1.16 | 0.97 |
| 2.74 | 2.53 |
| 2.35 | 2.09 |

It is evident from the above results, that the subject reagents can be employed in an accurate assay for IgA, the results tracking with a distinctively different technique.

Ex. 9. Preparation of Thiol Labeled Anti-AT (AT—$\alpha_1$-antitrypsin)

IgG fraction of goat anti-AT was obtained from Atlantic Antibody. The antibody was dialyzed overnight against 0.01 M PBS at pH 8.0. About 4.0 ml (11.6 mg/ml protein) were taken for labeling. The pH was adjusted downward to 7.4 by the addition of solid $KH_2PO_4$. A solution of 0.60 mg of S-acetylmercaptosuccinic anhydride in 50 μl dry DMF was added from a syringe while stirring. The addition took about 0.5 min. and the mixture stirred for an additional 3 min. Then 0.4 ml of 1 M $NH_2OH$ solution at pH 7-7.3 (obtained by neutralization 1 M $NH_2OH.HCl$ with 10 N NaOH) freshly prepared was added and the mixture stirred for another 3 min. The pH was lowered to 5.0 by the addition of solid citric acid and the reaction mixture dialyzed for 8 hrs. against 2 l of 0.1 M $KH_2PO_4$ (2 mM EDTA) which was degassed and saturated with argon (the dialysis Erlenmeyer was sealed during dialysis). Thiol groups were estimated by reacting 0.1 ml of the resultant solution with DTNB at pH 8.0. This indicated 1.8 SH groups per IgG. The labeled antibody was then immediately applied for reaction with the "activated" gel.

Ex. 10. Preparation of "Activated" Gel

The preparation of SH-Sepharose and reaction with DTNB were carried out as previously described. However, after reaction, the gel (2.5 ml) was packed in a column (0.6 cm in diameter) and separation of unreacted DTNB and wash were carried out on the column at a flow rate of 1-2 drops/10 sec.

Ex. 11. Coupling of Thiol Labeled Anti-AT to the Activated Gel

The thiol labeled antibody (3.9 ml) was circulated through the "activated" gel three times at the indicated flow rate. The gel was then washed with 0.1 M Tris-1M NaCl-2 mM EDTA at pH 8.0 until $OD_{280}$ of the wash was >>0.02. The unreacted antibody and wash were combined (15 ml) and dialyzed overnight against 0.01 M PBS at pH 8.0 in order to enable estimation of protein by UV. The results indicated 10.5 mg unbound protein, or about 34.8 mg antibody bound.

Ex. 12. Preparation of Fluorescein Labeled AT.

$\alpha_1$-Antitrypsin (AT) was obtained from Sigma

The material contained only 22-25% of AT as determined by RID (using Meloy kit) and assuming $E^{1\%}=5$. AT (15.4 mg) was dissolved in 1.2 ml of 0.1 M $NaHCO_3$ and labeled at pH 9.0 with 0.5 mg FITC as previously described. The resultant conjugate after separation on Sephadex G-25, was in 1.8 ml; $OD_{280}=9.8$, $OD_{496}=15.6$ (for fluorescein). AT was estimated by RID at 2.3-2.4 mg/ml.

Ex. 13. Absorption of Fluorescein Labeled AT by the Antibody Bound Gel and Elution of the AT:Anti-AT Complex The fluorescein labeled AT was passed two times through the anti-AT column. The column was then washed with 0.1 M Tris-1M NaCl-2mM EDTA at pH 8.0 until the eluent showed $OD_{276}<0.2$. The combined unbound AT and wash (5.0 ml) were applied for RID for determination of AT which gave 0.38 mg/ml. The column was further washed until $OD_{276}<<0.02$. Elution was then done with Tris buffer as above containing 8 mM of DTE. Fractions were collected when the yellow color of the simultaneously eluted 2-carboxy,4-nitrothiophenol appeared in the eluent. Three fractions each of 2.0 ml were collected and dialyzed overnight against 4 l of 0.01 M PBS at pH 8.0. Protein was estimated from the absorption spectra at 276 nm. AT was estimated from the fluorescein absorption at 495 nm, assuming the same ratio of $OD_{495}/OD_{276}$ for the eluted AT as for the crude AT before absorption, and $E^{1\%}=5$ for AT. The results obtained are shown in Table III.

TABLE III

| Fraction | Volume (ml) | $OD_{276}$ | $OD_{495}$ | AT (mg/ml) |
|---|---|---|---|---|
| 1 | 2 | 3.2 | 1.2 | 0.67* |
| 2 | 2 | 11.2 | 1.0 | 0.56 |
| 3 | 2 | 0.16 | 0.02 | 0.01 |
| total | | | | 1.24 |

*Quenching data suggest that less than 0.5 of the material in Fraction 1 is AT

Ex. 14. Preparation of Rhodamine-labelled Quencher Antibody

The IgG fraction of anti-AT (see Ex. 9 above) (1 ml) was dialyzed overnight against 0.5 l of 0.01 M PBS pH8.0. The concentration of protein was 11.5 mg/ml by UV ($E^{1\%}=14$). The protein was labeled with rhodamineisothiocyanate (0.85 mg), as previously described. The labeled antibody after separation on Sephadex LH-20 was in 1.7 ml.

Ex. 15. Standard Curve for AT and Assay

The 10 min. protocol described previously was used. Fluorescent working solution was prepared from fraction 2 diluted 1:10. The rhodamine-labelled anti-AT was diluted 1:4. Calibrators were prepared by serial dilutions of reference serum from Meloy. Frozen specimens were obtained and were assayed by RID using a kit from Behring Diagnostics. The specimens were allowed to stand overnight in the cold room, and were vortexed before assay.

In comparing the results, obtained in the fluorescence assay with RID over a concentration range of from about 0.005 to 1 mg/ml α-AT, the correlation was 0.96, slope 0.89.

Ex. 16. Preparation of Thiol labeled anti-C3

Goat IgG anti-C3 was obtained from Atlantic Antibody. About 6 ml were dialyzed overnight against 1 l of 0.01 M PBS at pH8.0 previously degassed and saturated with argon. The final volume was 7.2 ml and protein concentration estimated by UV ($E^{1\%}=14$) was 11.0 mg/ml. To a solution of 6 ml antibody (66 mg) was added solid $K_2HPO_4$ until the pH dropped to 7.4. A solution of 0.9 mg S-acetylmercaptosuccinic anhydride in 100 μl dry DMF was added (20 sec.) with vigorous stirring. After 3 min. a solution of 0.6 ml of 1 M $NH_2OH$ (pH 7-8) was added and stirred for an additional 3 min. The pH of the reaction mixture was then dropped to 5.0 by the addition of solid citric acid and immediately taken for dialysis. This was done in 1.8 l of 0.05 M $KH_2PO_4$-2 mM EDTA which was previously degassed, saturated with argon and kept sealed during dialysis (10 hrs).

Ex. 17. Coupling of Thiol Labeled Anti-C3 to the "Activated" Gel

Thiol gel (10 ml) was prepared and activated with 140 mg DTNB as previously described. The Thiol labeled antibody, after 10 hrs. of dialysis was added to the activated gel, followed by $H_2O$ (8-10 ml) until stirring of the mixture became possible. The pH of the mixture was adjusted to 8.0 by the addition of solid Tris base. The mixture was stirred very slowly overnight. Then it was packed in a column (0.9 cm diameter), and the buffer was eluted thus removing the unbound antibody. The column was then washed with 8 ml of 0.1 M Tris-1 M NaCl at pH8.0. The filtrate and wash were combined and dialyzed overnight against 2 l of 0.01 M PBS at pH8.0 to enable the estimation of unbound antibody. This resulted in a final volume of 22 ml with 0.47 mg/ml protein. The column was washed with additional 5 ml Tris/NaCl buffer, which showed $OD_{276}<0.02$. At that point the height of the gel in the column was 10 cm which corresponds to a volume of 8.6 ml.

Ex. 18 Preparation of Fluorescein-labelled C3 Fraction

A fraction of serum protein was prepared by precipitation with 5-12% PEG according to a known procedure (*Biochemistry*, 15, 4513 (1976)). Starting with 26 ml of pooled human serum (1 day old), and redissolving the precipitate in 20 ml of buffer (according to the procedure), gave a solution of $OD_{276}=20.75$. The C3 was estimated by use of a RID kit from Meloy at 1.4 mg/ml. Ten ml of the C3 protein was labelled with 4 mg of FITC at pH9.0 as previously described. After 2 hrs at room temperature the mixture was separated on Sephadex G-25 equilibrated with PMS-containing buffer at pH8.0. The resultant conjugate, 13.2 ml gave $OD_{276}=29.8$, $OD_{496}=31.6$ and 0.88 mg/ml of C3 by RID.

Ex. 19. Absorption of fluorescein labeled C3 by the antibody bound gel and elution of the C3:anti-C3 complex Fluorescein labeled C3 (12 ml) was passed twice through the affinity column (1 drop/5-10 sec.). The column was washed with 8 ml of 0.1 M Tris-1 M NaCl-2 mM EDTA at pH8.0, and the filtrate and wash were combined. RID determination of C3 in the combined solution (20 ml) showed 0.22 mg/ml. The column was further washed with 10 ml Tris buffer, which when pooled showed $OD_{276}=0.09$. Then the column was washed with 0.1 M $KH_2PO_4$-1 M NaCl which was adjusted to pH5.6 with 10 N NaOH. This acidic wash totaled 25 ml, of which the last 10 ml when pooled and adjusted to pH8.0 showed $OD_{276}<0.02$. Then Tris/NaCl buffer was passed through the column until the pH returned to 8.0. The C3 complex was then eluted with the same Tris/NaCl buffer containing 1 mg/ml of DTE. Fractions were collected at the appearance of yellow color in the eluent. All the fractions collected were dialyzed overnight against 0.01 M PBS-2 mM EDTA-0.05% NaN₃, at pH8.0. The fractions obtained are described in Table V.

TABLE V

| Fraction Number | Volume Collected (ml) | Volume After Dialysis | OD 496nm | OD 276nm |
|---|---|---|---|---|
| 1 | 1.0 | 1.0 | 0.09 | 0.20 |
| 2 | 1.0 | 1.0 | 0.22 | 1.11 |
| 3 | 0.7 | 1.0 | — | — |
| 4 | 1.0 | 1.0 | 0.51 | 1.54 |
| 5 | 4.9 | 6.5 | 2.31 | 11.55 |
| 6 | 1.0 | 1.0 | 0.12 | 0.39 |

Ex. 20. Preparation of Rhodamine Labeled Anti-C3

Anti-C3 (1.2 ml of 11.0 mg/ml) was labeled with 0.95 mg rhodamine in 30% glycerol as previously described. The labeled antibody was obtained in 2.0 ml.

Ex. 21 Standard Curve for C3 and Assay

The 10 min. protocol described previously was used. Fluorescent working solution was prepared from fraction #5 diluted 1:21. The rhodamine labeled antibody was diluted 1:6. Calibrators were prepared from Hyland reference serum. Specimens were diluted 1:13 before assay. The results obtained were compared with RID results using a Hyland kit. The results are as follows.

In assaying 36 samples by the fluorescent method previously described and a commercial RID method for C3, over a concentration range of about 60-160 mg/ml×10⁻², the correlation was 0.89, the slope was 0.89.

It is evident from the above results, that the subject compositions provide a simple and useful technique for concentrating antigen analytes of particular interest as fluorescent reagents, where the reagents may now be used in immunoassays for the determination of the analyte. When employed in immunoassays, the reagents are substantially free of the fluorescent signal label bonded to materials other than the analyte of interest. Therefore, background interference is minimized so as to provide for a more accurate and sensitive assay.

Although the foregoing invention has been described in some detail by way of illustration and example for purposes of clarity of understanding, it will be obvious that certain changes and modifications may be practiced within the scope of the appended claims.

What is claimed is:

1. A method for purifying labeled poly(amino acid) ligands for use in immunoassays, where the poly(amino acid) ligands which are labeled are present in a mixture and said labeled poly(amino acid) ligands are prepared by covalently labeling said mixture of compounds which includes said poly(amino acid) ligands, wherein said ligand is a member of a specific binding pair consisting of ligand and its reciprocal antiligand and said labeled poly(amino acid) ligand is substantially enriched relative to other labeled compounds in said mixture; said method comprising: affixing to a displaceable disulfide substituted support a mercapto substituted member of said specific binding pair by displacement of said disulfide to form a specific binding pair member affixed to said support through a disulfide linkage;

binding to said affixed specific binding pair member labeled reciprocal member of said specific binding pair from a mixture of other labeled material;

removing from said support non-specifically bound label; and cleaving said disulfide to obtain a labeled reagent useful in immunoassays.

2. A method according to claim 1, wherein said affixed specific binding pair member is antiligand.

3. A method according to claim 1, wherein said displaceable disulfide is an aryl disulfide.

4. A method according to claim 1, wherein said antiligand is a Fab fragment.

5. A method according to any of claims 1, 2, 3 or 4, wherein said label is a fluorescer.

6. A method for preparing fluorescer-labeled poly(amino acid) ligands for use in immunoassays, where the poly(amino acid) ligands are present in a mixture and said fluorescer-labeled poly(amino acid) ligands are prepared by covalently fluorescer labeling said mixture including said poly(amino acid) ligands wherein said labeled poly(amino acid) is substantially enriched relative to fluorescer label bound to other than said ligand in said mixture; said method comprising:

displacing an aryl disulfide substituted support with mercapto containing antiligand for said poly(amino acid) ligand to form an antiligand disulfide substituted support;

binding fluorescer labeled ligand from a mixture of other labeled material to said antiligand on said support;

removing from said support fluorescer label other than bound to ligand; and cleaving said disulfide to yield labeled ligand bound to antiligand enriched relative to label bound to other than ligand.

7. A method according to claim 6, wherein said support is a polysaccharide.

8. A method according to claim 6, wherein said fluorescer is a fluorescein.

9. In a method for performing an immunoassay involving labeled ligand and antiligand, the improvement which comprises employing as the labeled ligand a reagent prepared according to any of claims 1 or 6.

10. A method according to claim 9, wherein said label is a fluorescer.

* * * * *